United States Patent
Lary et al.

(10) Patent No.: US 7,314,466 B2
(45) Date of Patent: Jan. 1, 2008

(54) MINIMALLY INVASIVE VASCULAR SURGERY

(76) Inventors: G. Banning Lary, 6371 SW. 87th Ter., Miami, FL (US) 33143; Leonard Pinchuk, 13704 SW. 92 Ct., Miami, FL (US) 33176

( * ) Notice: Subject to any disclaimer, the term of this patent is extended or adjusted under 35 U.S.C. 154(b) by 425 days.

(21) Appl. No.: 10/901,409

(22) Filed: Jul. 27, 2004

(65) Prior Publication Data

US 2005/0074399 A1   Apr. 7, 2005

Related U.S. Application Data

(60) Provisional application No. 60/508,133, filed on Oct. 2, 2003.

(51) Int. Cl.
*A61M 31/00* (2006.01)
(52) U.S. Cl. .................................................. 604/507
(58) Field of Classification Search ................ 604/507, 604/508, 509, 510; 424/9.52, 1.21, 9.4, 9.6, 424/450
See application file for complete search history.

(56) References Cited

U.S. PATENT DOCUMENTS

| 4,039,665 | A | 8/1977 | Foley |
| 5,676,962 | A | 10/1997 | Cabrera Garrido et al. |
| 6,331,289 | B1 * | 12/2001 | Klaveness et al. ......... 424/9.52 |
| 6,572,873 | B1 | 6/2003 | Osman et al. |
| 6,726,674 | B2 | 4/2004 | Leu |

* cited by examiner

*Primary Examiner*—Manuel Mendez
(74) *Attorney, Agent, or Firm*—McHale & Slavin, P.A.

(57) ABSTRACT

A mixture for intravenous injection to treat damaged vascular structures contains a mixture of carbamide peroxide and a sclerosing agent. The injected mixture expresses blood from the affected vascular structure by formation of bubbles, in situ. The bubbles carry the sclerosing agent into contact with the lining of the vascular structure resulting in destruction. The size of the bubbles may be varied by adding hydrogen peroxide and varying the proportions of carbamide peroxide and hydrogen peroxide in the mixture.

6 Claims, No Drawings

MINIMALLY INVASIVE VASCULAR SURGERY

RELATED APPLICATIONS

This application claims priority under 35 USC 119(e) to the Provisional Patent Application, 60/508,133, filed Oct. 2, 2003.

BACKGROUND OF THE INVENTION

1. Field of the Invention

This invention relates to the field of minimally invasive reduction of tubular structures in the body, specifically portions of the vasculature.

2. Description of the Prior Art

There are several kinds of vascular damage due to disease, injury, or genetics, some of which are normally visible, and described as venous blemishes, spiders, sunbursts, telangiectases, venous plexi, and groups of dilated venules, all of which can be included in the term varicose veins. They are considered to be the result of incompetent valves within the lumen of the veins and occur, primarily, in the legs. The varicose veins are subcutaneous and appear as tortuous distended lumps that vary greatly in diameter, appearance, lengths and numbers. Conventional treatments are vein stripping and sclerotherapy.

Sclerotherapy involves injecting a sclerosing agent into the lumen of an isolated portion of a vein. This results in damage to the lining, called the intima, with clotting of blood inside the vein lumen. The clot becomes liquid due to fibrinolytic enzymes. The fluid in the vein is concentrated with the brown pigment, hemosiderin, and other particles and chemicals. Osmosis of perivenous fluids then occurs through the walls of the vein into the liquified clot. This results in an increased hydrostatic pressure within the vein. This pressure forces the liquified fluid within the vein to transgress through the dead wall into surrounding tissues. The fluid is rapidly absorbed in the perivenous tissues. However, the hemosiderin deposits may remain for long periods causing an unsightly, "staining," or long term pigmentation that is distressing to the patient. Some stains may gradually disappear by phagocytosis and by the natural slow desquamation of the skin but some may become permanent. External pressure to collapse the veins and subsequent needle perforations for evacuations of the liquified clot help decrease the staining but are painful and time consuming.

Foley, U.S. Pat. No. 4,039,665 issued Aug. 2, 1977, discloses clearing the afflicted vein of blood by injecting small amounts of air into the lumen before applying a 20% saline solution with heparin as a sclerosing agent.

Cabrera Garrido et al, U.S. Pat. No. 5,676,962 issued Oct. 14, 1997, discloses injecting a microfoam into the lumen to displace the blood and apply the sclerosing agent. The foam is a combination of the sclerosing agent and pressurized oxygen beaten until the foam is formed. The sclerosing agent may be polydocanol, sodium tetradecyl sulfate, hypertonic glucostated solution, chromated glycerol or others.

Osman et al, U.S. Pat. No. 6,572,873 issued Jun. 3, 2003, discloses another microfoam with 50% oxygen or carbon dioxide and polidocanol or sodium tetradecyl sulfate.

Leu, U.S. Pat. No. 6,726,674 issued Apr. 27, 2004, discloses a catheter for injecting sclerosing agents. The catheter has an inflatable balloon with perforations in the balloon for delivery of the agent to the lumen of the vein.

The injection of foams is limited to a certain sized needle or catheter based on maintaining the cellular structure of the foam thereby limiting the size vein that can be treated. The injection of a liquid sclerosing solution results in a mixing of the blood and the solution in the lumen with residual amounts of blood remaining in the vein.

What is needed in the art is a treatment that will force the blood from any sized vein and place the sclerosing agent in contact with the vein wall.

SUMMARY OF THE PRESENT INVENTION

Disclosed is a method of treating damaged vasculature in the body by the steps of: preparing a mixture of an amount of carbamide peroxide and an amount of sclerosing agent, and injecting the mixture into the vasculature of the body whereby bubbles form in the vasculature removing blood therefrom and bringing the sclerosing agent in contact with the vasculature. The intravenous injection to treat damaged vascular structures contains a mixture of carbamide peroxide and a sclerosing agent. The injected mixture expresses blood from the affected vascular structure by the use of the bubbles, in situ. The bubbles carry the sclerosing agent into contact with the lining of the vascular structure resulting in destruction. The size of the bubbles may be varied by adding hydrogen peroxide and varying the proportions of carbamide peroxide and hydrogen peroxide in the mixture.

Therefore, it is an objective of this invention to teach a minimally invasive treatment for destroying damaged veins without residual visible effects.

It is another objective of this invention to teach treatment of damaged veins based on the injection of a solution to exhaust blood from the damaged vein and administer an active agent.

It is yet another objective of this invention to teach a solution for injection into veins that will foam in situ and apply a sclerosing agent.

Other objectives and advantages of this invention will become apparent from the following description wherein are set forth, by way of illustration and example, certain embodiments of this invention.

DETAILED DESCRIPTION OF THE INVENTION

This minimally invasive treatment of certain veins or portions of veins relies partly on a reaction of the of the composition administered into the vein and an enzyme naturally present in the vein. The treatment may be applied to the vasculature to ameliorate a condition generally referred to as varicose veins though other vascular conditions, such as hemorrhoids, are contemplated. Also, the treatment may be used to close a vessel as part of a re-vascularization of diseased or traumatized blood vessels.

The composition includes mixtures of carbamide peroxide or urea hydrogen peroxide, and a sclerosing agent, such as sodium tetradecyl sulfate. Other known sclerosing agents may be substituted for the tetradecyl sulfate or added to the composition.

The extremely powerful enzyme, catalase, occurs naturally in most human tissues and is present in the peroxisomes of nearly all aerobic cells. It protects the cells from the toxic effects of peroxide by catalyzing it to decompose to water and oxygen.

The following is one explanation of the probable biochemical reactions resulting in the efficacy of this treatment, though other explanations may later be determined to be correct. Upon administration of a solution of sclerosing agent and carbamide peroxide to the lumen of a vein, the catalase will act to dissociate the carbamide peroxide into water, nascent oxygen and urea. Most of the oxygen would rapidly become oxyhemoglobin by combining with the hemoglobin in the blood. The nascent oxygen, being unstable, would bubble off as gaseous oxygen. These bubbles would act to clear the fluid blood and hemosiderin from the vein. The sclerosing agent would not appear to be affected by this reaction and would be carried by the bubbles to contact the endothelium of the lining of the vein to eventuate in sclerosis and subsequent replacement with fibrous tissue.

These observations resulted from an experiment using a mixture of 3% solution sodium tetradecyl sulfate and a 10% solution of carbamide peroxide or urea hydrogen peroxide, injected by hypodermic syringe into a sample of heparinized human venous blood contained in a small plastic tube. Upon injection of the mixture there was an immediate dissociation of the blood/agent solution with the formation of visible bubbles. The dark blood immediately changed to a bright red, presumably due to the formation of oxyhemoglobin. The bubbles replaced most of the blood as determined by the visible outline of the bubbles and the movement of the blood out the other end of the tubing. The bubbles were small, on the order of 0.5 mm, in size but it is considered that such a treatment would be effective in very small veins or small telangiectsaia.

It was determined that larger bubbles would increase the efficacy for treatment of larger veins and vessels. To generate more and larger bubbles, a solution of hydrogen peroxide was added to the carbamide peroxide. A mixture of the carbamide peroxide and hydrogen peroxide was injected into a vial of prepared blood. This resulted in the blood rapidly being replaced by large bubbles with the blood rapidly expressed from the open end of the tube. Some small bubbles were present but overshadowed by the large bubbles which indicates that both the carbamide peroxide and the hydrogen peroxide contribute to the enzymatic reaction.

In order to control bubble size, other mixtures of carbamide peroxide, hydrogen peroxide and tetradecyl sulfate were prepared. A mixture of three drops of hydrogen peroxide, five drops of carbamide peroxide and 3 mm of tetradecyl sulfate was added to 5 mm of water and injected into a plastic tube partially filled with heparinized blood. This resulted in 95% of the blood being washed out of the tube with bubble size being larger than the carbamide peroxide, alone, and smaller than the carbamide peroxide and hydrogen peroxide solution. The bubble size was on the order of 1 mm with some small bubbles present. By adjusting the proportions of the carbamide peroxide and the hydrogen peroxide in the solution, the size of the bubbles can be varied.

Further, it was noted that the bubbles within the tube apparently created a higher coefficient of friction with the wall of the tubing that prevented the blood from returning to the original lumen when the tubing was elevated to increase the pressure.

A number of embodiments of the present invention have been described. Nevertheless, it will be understood that various modifications may be made without departing from the spirit and scope of the invention. Accordingly, it is to be understood that the invention is not to be limited by the specific illustrated embodiment but only by the scope of the appended claims.

What is claimed is:

1. A method of treating certain selected damaged vasculature including varicose veins or portions of certain selected varicose veins in the body comprising the steps of
   a) preparing a mixture of an amount of carbamide peroxide and an amount of sclerosing agent,
   b) isolating said certain selected damaged vasculature including said varicose veins, or portions of said certain selected varicose veins in the body, and
   c) injecting said mixture in said isolated certain selected damaged vasculature including varicose veins, or portions thereof, whereby bubbles form in said certain selected damaged vasculature removing blood therefrom and bringing said sclerosing agent in contact with said certain selected damaged vasculature including varicose veins or portions thereof.

2. A method of treating said certain selected damaged vasculature in accordance with claim 1 further comprising:
   a) adding an amount of hydrogen peroxide to said mixture.

3. A method of treating said certain selected damaged vasculature in accordance with claim 2 further comprising:
   a) varying said amount of hydrogen peroxide in said mixture thereby varying the size of said bubbles.

4. A method of treating said certain selected damaged vasculature in accordance with claim 3 further comprising:
   a) varying said amount of carbamide peroxide thereby varying the size of said bubbles.

5. A method of treating said certain selected varicose veins in accordance with claim 1 further comprising providing tetradecyl sulfate as said sclerosing agent.

6. A method of treating said certain selected varicose veins in accordance with claim 5 further comprising providing an amount of hydrogen peroxide.

* * * * *